US005328928A

United States Patent [19]

Addor et al.

[11] Patent Number: 5,328,928

[45] Date of Patent: Jul. 12, 1994

[54] N-ACYLATED ARYLPYRROLES USEFUL AS INSECTICIDAL, AGENTS

[75] Inventors: Roger W. Addor, Pennington, N.J.; Stephen F. Donovan; Robert E. Diehl, both of Yardley, Pa.; Kenneth A. Kremer, Lawrenceville, N.J.

[73] Assignee: American Cyanamid Company, Wayne, N.J.

[21] Appl. No.: 80,886

[22] Filed: Jun. 22, 1993

Related U.S. Application Data

[63] Continuation of Ser. No. 763,715, Sep. 23, 1991, abandoned, which is a continuation-in-part of Ser. No. 522,299, May 11, 1990, abandoned.

[51] Int. Cl.$^5$ .................... A61K 31/40; C07D 207/34; C07D 207/337

[52] U.S. Cl. .................................. 514/423; 514/277; 514/422; 514/427; 514/429; 546/275; 546/283; 546/284; 548/406; 548/517; 548/518; 548/539

[58] Field of Search ............... 514/277, 422, 423, 427, 514/429; 546/275, 283, 284; 548/406, 517, 518, 527, 539

[56] References Cited

U.S. PATENT DOCUMENTS 4,963,181 10/1990 Wollweber et al. ................ 548/430
5,157,047 10/1992 Kameswaran et al. ............. 514/423
5,171,355 12/1992 Negele et al. ........................... 71/95

FOREIGN PATENT DOCUMENTS 0019939 of 1968 Japan .

*Primary Examiner*—Mukund J. Shah
*Assistant Examiner*—Y. N. Gupta
*Attorney, Agent, or Firm*—John W. Hogan, Jr.

[57] ABSTRACT

This invention provides new N-acylated arylpyrroles effective for the control of insects, acarids, nematodes, fungi and mollusks and useful for the protection of growing plants from the destructive actions of said pests. The invention also provides pesticidal compositions containing the new N-acylated arylpyrroles and methods for the preparation of thereof.

17 Claims, No Drawings

N-ACYLATED ARYLPYRROLES USEFUL AS INSECTICIDAL, AGENTS

This is a continuation of co-pending application Ser. No. 07/763,715, filed on Sep. 23, 1991, now abandoned, which is a continuation-in-part of application Ser. No. 07/522,299, filed on May 11, 1990, now abandoned.

DESCRIPTION OF THE INVENTION

This invention relates to new N-acylated aryl pyrroles depicted by formula I:

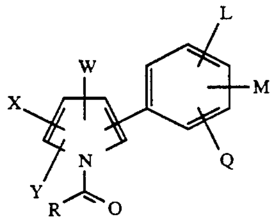

(I)

wherein

X is F, Cl, Br, I or $CF_3$;

Y is F, Cl, Br, I or $CF_3$;

W is CN or $NO_2$;

L is H, F, Cl or Br; and

M and Q are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$;

and when M and Q are attached to adjacent carbons in the phenyl ring and taken with the carbon atoms to which they are attached, they may form a ring in which MQ represents the structure:

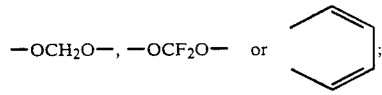

Z is S(O)n or O;

$R_1$ is H, F, $CHF_2$, CHFCl or $CF_3$;

$R_2$ is $C_1$-$C_3$ alkyl, $C_1$-$C_3$ alkoxy or $NR_3R_4$;

$R_3$ is H or $C_1$-$C_3$ alkyl;

$R_4$ is H, $C_1$-$C_3$ alkyl or $R_5CO$;

$R_5$ is H or $C_1$-$C_3$ alkyl; and n is an integer of 0, 1 or 2; and

R is phenyl optionally substituted with one to three three halogen atoms, one to three $C_1$-$C_4$ alkyl groups, one $C_5$-$C_{12}$ alkyl group, one to two $C_1$-$C_4$ alkoxy groups, or one phenoxy, $C_1$-$C_4$ alkylthio, trialkylsilyl, $C_1$-$C_4$ alkylsulfinyl, $C_1$-$C_4$ alkylsulfonyl, carbo-$C_1$-$C_4$-alkoxy, carboxy, $CF_3$, CN, $NO_2$, di($C_1$-$C_4$ alkyl)amino, or $C_1$-$C_4$ alkanoylamino;

1-naphthyl or 2-naphthyl;

2-, 3- or 4-pyridyl optionally substituted with one to three halogen atoms; or a heteroaromatic 5-membered ring containing an oxygen, nitrogen, or a sulfur atom, and optionally substituted with one to three halogen atoms.

A preferred group of compounds of this invention are depicted by the structural formula II, which may be illustrated as follows:

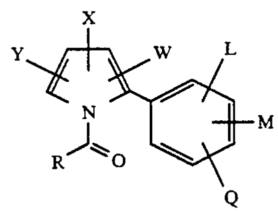

(II)

wherein L, M, Q, W, X, Y and R are as described for formula I above.

Another preferred group of compounds of this invention have the structure of formula II, where W is CN; X is F, Cl, Br or $CF_3$; Y is Cl, Br or $CF_3$; L is H, F, Cl or Br; M and Q are each independently H, halogen or $CF_3$; and R is phenyl optionally substituted with one to three halogen atoms, one to three $C_1$-$C_4$ alkyl groups, one to two $C_1$-$C_4$ alkoxy groups, or one $C_1$-$C_4$ alkylthio, trialkylsilyl, carbo-$C_1$-$C_4$-alkoxy, carboxy, $CF_3$, CN, $NO_2$ or di($C_1$-$C_4$ alkyl)amino;

1-naphthyl or 2-naphthyl;

2- or 3-furyl; or

2-, 3- or 4-pyridyl optionally substituted with one to three halogen atoms.

Advantageously, the N-acylated arylpyrroles of this invention, as depicted by formula I, can be prepared from the appropriately substituted arylpyrrole, described in U.S. patent application Ser. No. 392,495, filed Aug. 11, 1989 and incorporated herein by reference thereto.

Preparation of the N-acylated arylpyrroles of the invention generally involves the acylation of an arylpyrrole having the formula III structure:

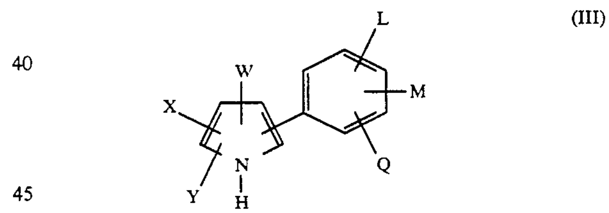

(III)

wherein L, M, Q, W, X and Y are as described for formula I above.

Acylation of the formula III arylpyrrole can be achieved by the reaction of said formula III arylpyrrole with an alkali metal hydride or alkali metal t-butoxide and an acylating agent having the structure: RCOCl wherein R is as described above.

In the reaction the alkali metal hydride or alkali metal t-butoxide is generally dispersed in an anhydrous organic solvent such as dry tetrahydrofuran, dimethoxyethane, dimethylformamide, dimethylsulfoxide, or the like, and the thus formed mixture then heated to refluxing temperature. The reaction mixture is then cooled, generally to between 20° C. and 30° C., and the acylating agent, RCOCl, wherein R is as described above, added to said mixture. Thereafter, the thus prepared mixture is heated to refluxing temperature until the N-acylated arylpyrrole is formed. The reactions are preferably conducted under a blanket of inert gas such as nitrogen or argon. The reactions may be illustrated as follows:

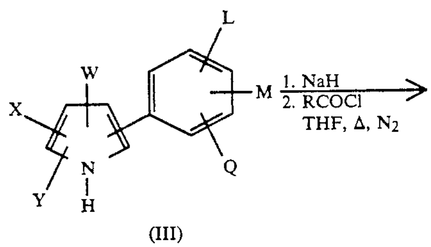

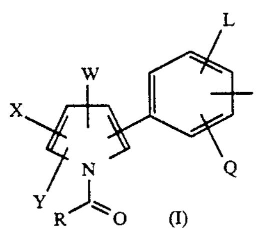

The formula I N-acylated arylpyrroles of this invention are effective for the control of a wide variety of destructive plant pests that ravage all types of vegetation including field crops, forage crops, cotton, cucurbits, cereal grains, ornamentals, cole crops, shrubs and the like.

Among these destructive pests are the insects and acarina that feed upon the foliage, stems, fruits, flowers and sap of plants. These insects and acarina are generally of the orders: Coleoptera, Diptera, Thysanoptera, Homoptera, Hymenoptera, Lepidoptera and Orthoptera. Other pests that are destructive to plant life, but are readily controlled with the formula I N-acylated arylpyrroles of this invention, are soil-borne pests such as nematodes, rootworms, wireworms and the like which attack and destroy the root systems of plants and mollusks, particularly of the class gastropada, which includes slugs, cowries, limpets and snails, that are voracious feeders with an appetite for seedling plants, especially ornamentals. It is further found that the N-acylated arylpyrroles of this invention have the added advantage that they may also be used for the control of fungal organisms and the protection of plants against the ravages of fungal diseases.

To achieve control of the above-said pests and/or provide protection of plants from attack thereby, it has been found that the N-acylated arylpyrroles of this invention can be prepared in the form of aqueous or liquid formulations and applied to the plants and/or soil in which they are growing as an aqueous or liquid spray or drench containing from about 10 ppm to about 10,000 ppm and preferably about 50 ppm to 4000 ppm of the formula I N-acylated arylpyrrole. These liquid compositions are usually applied in sufficient amount to provide about 0.1 kg/ha to about 4.0 kg/ha of the active ingredient to the locus of treatment.

They may also be prepared as solid formulations such as compacted granules, dusts, dust concentrates and bait formulations which may be applied to the soil in which plants are to be protected, or, in the case of dusts or dust concentrates they may be applied to the foliage of plants.

The aqueous or liquid compositions useful in the practice of this invention may be initially formulated as a solid or liquid concentrate which is dispersed in water or other inexpensive liquid diluent, generally at the locus of treatment, for spray or drench application.

The concentrates useful for preparation of sprays or drenches may take the form of a wettable powder, emulsifiable concentrate, aqueous flowable or water dispersible granular formulation.

A typical suspension concentrate formulation may be prepared by grinding together about 5% to 25% by weight of a formula I N-acylated arylpyrrole, about 3% to 20% by weight of an anionic surfactant such as dodecyl benzene sulfonic acid, about 1% to 5% by weight of a nonionic surfactant such as an ethylene oxide block copolymer having about 8 to 11 mols of ethoxylation, about 1% to 5% by weight of an alkylphenol polyethylene oxide condensate with 9 to 10 mols of ethoxylation and q.s. to 100% with a petroleum aromatic solvent.

A preferred group of ethylene oxide/propylene oxide block copolymers for use in the compositions of this invention are butyl-omega-hydroxypoly(oxypropylene)-block polymer with poly(oxyethylene) having an average molecular weight in a range of 2,400 to 3,500, with alpha-butyl-omega-hydroxy-ethylene oxide-propylene oxide block copolymers having an HLB of 12 and a viscosity at 25° C. of 2000 CPS, (TOXIMUL® 8320, Stepan Chemical Co.) being a most preferred member of this class of emulsifiers.

Preferred alkylphenol polyethylene oxide condensates for use in the compositions of the invention are the nonylphenol ethoxylates, with nonylphenol ethoxylate (9 to 10 mols of ethylene oxide) (FLO MO® 9N, DeSoto, Inc. Sellers Chemical Div.) being a most preferred member of this class of emulsifiers.

Among the preferred petroleum aromatic solvents useful in the preparation of suspension concentrates containing the formula I N-acylated arylpyrroles of the present invention are:

1) aromatic hydrocarbon mixture ($C_9$ to C12 aromatics, distillation range 183°-210° C.) (AROMATIC® 150, Exxon)
2) aromatic hydrocarbon mixture ($C_8$ to $C_9$ aromatics, distillation range 155°-173° C.) (AROMATIC® 100, Exxon)
3) aromatic hydrocarbon mixture ($C_{10}$ to $C_{13}$ aromatics, distillation range 226°-279° C.) (AROMATIC® 200 )
4) aromatic hydrocarbon mixture ($C_8$ to $C_9$ aromatics, bp 148.9° C.) (TENNECO® T500/100) aromatic hydrocarbon mixture (TENNECO® T400) hydrocarbon mixture, (distillation range 177°-277° C.) (HAN® Exxon)
5) aromatic hydrocarbon mixture (distillation range 210°-288° C.) (PANASOL® AN-3N, Amoco)
6) aromatic hydrocarbon mixture (distillation range 179°-216° C.) (Shell CYCLO SOL® 63)

Flowable formulations can be prepared by admixing about 5% to 50% and preferably about 10% to 25% by weight of the formula I N-acylated arylpyrrole with about 2% to 3% by weight of a naphthalene sulfonic condensate, about 0.1% to 0.5% by weight of a nonionic nonylphenoxy polyethoxy ethanol, about 0.1% to 0.5% of xanthum gum, about 0.1% to 0.5% of a swelling clay such as bentonite, about 5% to 10% by weight of propylene glycol, about 0.1% to 0.5% by weight of a silicone antifoam agent, about 0.1% to 0.3% by weight of an aqueous dipropylene glycol solution of 1,2-benzisothiazolin-3-one (preservative) and q.s. to 100% with water.

A wettable powder can be prepared by grinding together about 5% to 25% by weight of the formula I N-acylated arylpyrrole about 3% to 15% by weight of an anionic surfactant, such as dodecylbenzene sulfonic acid, about 3% to 10% of a nonionic ethylene oxide block copolymer, about 1% to 3% by weight of a nonylphenol ethoxylate having 8 to 11 mols of ethoxylation and about 47% to 88% by weight of an inert solid diluent such as montmorillonite, attapulgite, diatomaceous earth, talc or the like.

In addition to the suspension concentrates, aqueous flowables and wettable powders described hereinabove, other formulations such as water dispersible granules, emulsifiable concentrates and compacted granular formulations may also be prepared and used to protect plants from attack by the pests mentioned above.

Surprisingly, the N-acylated arylpyrrole compounds of the present invention provide plant-safe products. Danger of in-situ hydrolytic generation of certain phytotoxic N-H arylpyrrole compounds is slight. For example, 1-benzoyl-4-bromo-2-(p-chlorophenyl)-5-(trifluoromethyl)pyrrole-3-carbonitrile is found to have a half-life in a homogeneous water-acetonitrile mixture measured in years.

In sharp distinction to compounds of the present invention, certain fully substituted N-alkanoyl arylpyrrole compounds are less hydrolytically stable. Danger of in-situ generation of certain phytotoxic N-H arylpyrrole compounds in significantly greater than for the N-acylated arylpyrrole compounds of the present invention. For example, 1-acetyl-4-bromo-2-(p-chlorophenyl)-5-(trifluoromethyl)pyrrole-3-carbonitrile is found to have a half-life in a homogeneous water-acetonitrile mixture measured in hours.

These and other advantages of the invention may become more obvious from the examples setforth below. These examples are provided simply for illustrative purposes and are not intended as limitations of the invention.

EXAMPLE 1

Preparation of 1-Benzoyl-4-bromo-2-chloro-5-(p-chlorophenyl ) pyrrole-3 -carbonitrile

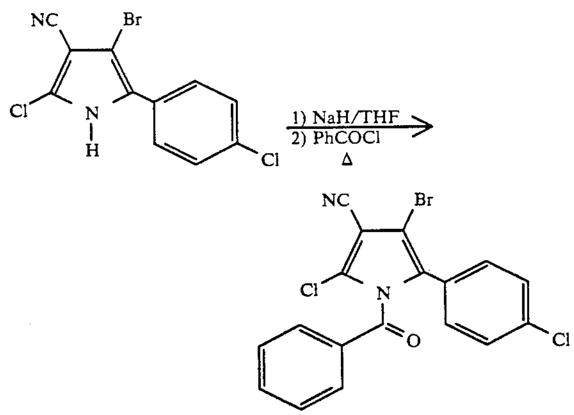

To a suspension of sodium hydride (0.21 g of a 60% dispersion, 5.3 mmol) in 50 mL of dry tetrahydrofuran in a 100 mL single neck round bottom flask fitted with a condenser and a nitrogen inlet is added portionwise 4-bromo-2-chloro-5-(p-chlorophenyl)pyrrole-3-carbonitrile (1.0 g, 3.2 mmol). The reaction is stirred for 15 minutes at room temperature before the pipette addition of hexamethylphosphoramide (HMPA) (3 mL) followed immediately by benzoyl chloride (0.75 g, 5.4 mmol). Thereafter the reaction mixture is heated to reflux for 17 hours and allowed to cool. Rotary evaporation yields a crude semi-solid to which is added 15 mL of diethyl ether and 15 mL of water. Vigorous stirring over a period of 20 minutes followed by vacuum filtration results in the isolation of the product as a yellow solid (1.0 g, 2.4 mmol, 75%), mp 179°-181° C.

EXAMPLE 2

Preparation of 1-Benzoyl-4-bromo-2- (p-chlorophenyl) -5-(trifluoromethyl)pyrrole-3-carbonitrile

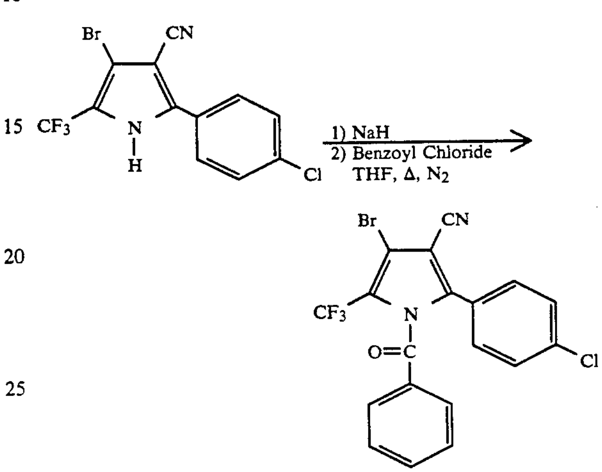

To a 250 mL round bottom flask, equipped with a magnetic stirrer and a condenser with a nitrogen adapter, is added 0.60 g. NaH (60%). The NaH is washed with ca. 50 mL hexanes, the hexanes are decanted, and replaced with 75 ml tetrahydrofuran (THF). There is some bubbling upon the addition of the THF, therefore the THF is not quite anhydrous. The flask is cooled in an ice-water bath and 2.04 g of 4-bromo-2-(p-chlorophenyl)-5-(trifluoromethyl)pyrrole-3-carbonitrile is added in portions with the evolution of hydrogen. The reaction mixture is refluxed for 20 minutes, cooled to ca. room temperature and then 2.3 mL benzoyl chloride is added and the reaction mixture is refluxed overnight. The reaction is cooled and poured into ca. 100 mL of cold water and extracted with 100 mL ether. The ether extract is washed with 100 mL water, 100 mL saturated $NaHCO_3$, dried over $K_2CO_3$, filtered, and concentrated on a rotary evaporator under reduced pressure. The excess benzoyl chloride is removed by distillation with a kugelrohr apparatus at 100° C. at −5 mm Hg. Then the residue is refluxed with 100 mL hexanes, and filtered warm to remove most of the unreacted 4-bromo-2-(p-chlorophenyl)-5-(trifluoromethyl)pyrrole-3-carbonitrile. The reaction product is then chromatographed on a "flash" silica gel column ca. 1" by 12" eluted by 10% ethyl acetate and 90% hexanes. Then 100 mL fractions are collected and fractions #3 and #4 are combined and concentrated on a rotary evaporator under reduced pressure. Then 50 mL hexanes are added, the mixture is refluxed to bring the product into solution and the solution allowed to slowly crystallize overnight. After filtration 1.58 grams of white crystals of 1-benzoyl-4-bromo-2-(p-chlorophenyl)-5-(trifluoromethyl)pyrrole-3-carbonitrile are isolated. Melting point 105°-107° C.

Following the above procedure, but substituting the appropriate arylpyrrole for 4-bromo-2-(p-chlorophenyl)-5-(trifluoromethyl)pyrrole-3-carbonitrile and the appropriate acylhalide RCOCl for benzoyl chloride yields the following compounds.

4-bromo-2-(p-chlorophenyl)-1-o-toluoyl-5-(trifluoromethyl)pyrrole-3-carbonitrile M.P. 131.5°-134.5° C.;

4-bromo-1-(m-chlorobenzoyl)-2-(p-chlorophenyl)-5-(trifluoromethyl)pyrrole-3-carbonitrile M.P. 88°-90° C.;

4-bromo-2-(p-chlorophenyl)-1-(2-furoyl)-5-(trifluoromethyl)pyrrole-3-carbonitrile M.P. 152°-156° C.;

4-bromo-2-(p-chlorophenyl)-1-p-toluoyl-5-(trifluoromethyl)pyrrole-3-carbonitrile M.P. 113°-116.5° C.;

4-bromo-2-(p-chlorophenyl)-5-(trifluoromethyl)-1-(α,α,-α-trifluoro-p-toluoyl)pyrrole-3-carbonitrile; M.P. 110°-118° C.

4-bromo-2-(p-chlorophenyl)-1-(p-nitrobenzoyl)-5-(trifluoromethyl)pyrrole-3-carbonitrile M.P. 128°-132° C.;

4-bromo-1-(p-chlorobenzoyl)-2-(p-chlorophenyl)-5-(trifluoromethyl)pyrrole-3-carbonitrile M.P. 115°-117° C.;

4-bromo-2-(p-chlorophenyl)-1-(1-naphthoyl)-5-(trifluoromethyl)pyrrole-3-carbonitrile M.P. 101°-108° C.;

4-bromo-2-(p-chlorophenyl)-1-(m-fluorobenzoyl)-5-(trifluoromethyl)pyrrole-3-carbonitrile M.P. 111°-118° C.;

4-bromo-2 -(p-chlorophenyl)-1-(3,4-dichlorobenzoyl)-5-(trifluoromethyl)pyrrole-3-carbonitrile M.P. 135°-144° C;

1-benzoyl-4,5-dichloro-2-(3,4-dichlorophenyl)pyrrole-3-carbonitrile M.P. 141°-144° C.;

4-bromo-1-(p-tert-butylbenzoyl)-2-(p-chlorophenyl)-5-(trifluoromethyl)pyrrole-3-carbonitrile M.P. 113°-115.5° C.;

1-benzoyl-4-bromo-2-(p-bromophenyl)-5-(trifluoromethyl)pyrrole-3-carbonitrile M.P. 112°-117° C.;

1-benzoyl-2,4-dichloro-5-(3,4-dichlorophenyl)pyrrole-3-carbonitrile M.P. 107°-110° C.;

1-benzoyl-2,4-dichloro-5-(2-naphthyl)pyrrole-3-carbonitrile M.P. 168°-173.5° C.;

4-bromo-2-(p-chlorophenyl)-1-(6-chloronicotinoyl)-5-(trifluoromethyl)pyrrole-3-carbonitrile M.P. 113°-115° C.;

4-bromo-2-(p-chlorophenyl)-1-picolinoyl-5-(trifluoromethyl)pyrrole-3-carbonitrile M.P. 114°-116° C.;

1-benzoyl-4-bromo-2-(3,4-difluorophenyl)-5-(trifluoromethyl)pyrrole-3-carbonitrile M.P. 72°-88° C.; or 1-benzoyl-4,5-dichloro-2-(α,α,α-trifluoro-p-tolyl)-pyrrole-3-carbonitrile M.P. 137.5°-139° C.

EXAMPLE 3

Insecticidal and acaricidal evaluations of N-acylated arylpyrroles

In these tests evaluations are performed using technical material dissolved in 50/50 acetone water mixtures. All concentrations reported herein are in terms of active ingredient. All tests are conducted in a laboratory maintained at about 27° C. The rating system employed is as follows:

| Rating System |
|---|
| o = no effect |
| 1 = 10-25% kill |
| 2 = 26-35% kill |
| 3 = 36-45% kill |
| 4 = 46-55% kill |
| 5 = 56-65% kill |
| 6 = 66-75% kill |
| 7 = 76-85% kill |
| 8 = 86-99% kill |
| 9 = 100% kill |

Where two or more tests are conducted using the same compound, the average of test results is reported.

The test species of insects and acarids used in the present evaluations along with specific test procedures are described below.

*Heliothis virescens,* 3rd instar tobacco budworm

Cotton cotyledons are dipped in the test solution and allowed to dry in a hood. When dry, each is cut into quarters and ten sections placed individually in 30 mL plastic medicine cups containing a 5-7 mm long piece of damp dental wick. One third-instar caterpillar is added to each cup and a cardboard lid placed on the cup. Treatments are maintained for 3 days before mortality counts and estimates of reduction in feeding damage are made.

*Spodoptera eridania,* 3rd instar larvae, southern armyworm

A Sieva lima bean leaf expanded to 7-8 cm in length is dipped in the test solution with agitation for 3 seconds and placed in a hood to dry. The leaf is then placed in a 100×10 mm petri dish containing a damp filter paper on the bottom and ten 3rd instar caterpillars. The dish is maintained for 5 days before observations are made of mortality, reduced feeding, or any interference with normal moulting.

*Spodoptera eridania,* 7-day residual

The plants treated in the above Test are maintained under high intensity lamps in the greenhouse for 7 days. These lamps duplicate the effects of a bright sunny day in June in New Jersey and are kept on for 14 hour day length. After 7 days, the foliage is sampled and assayed as in the above-said Test.

*Diabrotic undecimpunctata howardi,* 3rd instar southern corn rootworm

One cc of fine talc is placed in a 30 mL wide-mouth screw-top glass jar. One mL of the appropriate acetone solution is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

*Tetranychus urticae* (P-resistant strain), 2-spotted spider mite

Sieva lima bean plants with primary leaves expanded to 7-8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test solution for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

*Empoasca abrupta*, adults, western potato leafhopper

A Sieva lima bean leaf about 5 cm long is dipped in the test solution for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

Blattella germanica, residue test, adult male German cockroach

One mL of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

In these evaluations X×Test was not completed; −×Test could not be conducted; a blank means Test was not conducted and *=Data not yet reported.

Data obtained are reported in Table I below.

Compounds evaluated in these tests include:

| Compound # | Compound Name |
|---|---|
| 1 | 1-Benzoyl-4-bromo-2-(p-chlorophenyl)-5-(trifluoromethyl)pyrrole-3-carbonitrile M.P. 105–107° C.; |
| 2 | 4-bromo-2-(p-chlorophenyl)-1-o-toluoyl-5-(trifluoromethyl)pyrrole-3-carbonitrile M.P. 131.5–134.5° C.; |
| 3 | 4-bromo-1-(m-chlorobenzoyl)-2-(p-chlorophenyl)-5-(trifluoromethyl)pyrrole-3-carbonitrile M.P. 88–90° C.; |

-continued

| Compound # | Compound Name |
|---|---|
| 4 | 4-bromo-2-(p-chlorophenyl)-1-(2-furoyl)-5-(trifluoromethyl)pyrrole-3-carbonitrile M.P. 152–156° C.; |
| 5 | 4-bromo-2-(p-chlorophenyl)-1-p-toluoyl-5-(trifluoromethyl)pyrrole-3-carbonitrile M.P. 113–116.5° C.; |
| 6 | 4-bromo-2-(p-chlorophenyl)-5-(trifluoromethyl)-1-(α,α,α-trifluoro-p-toluoyl)-pyrrole-3-carbonitrile M.P. 110–118° C.; |
| 7 | 4-bromo-2-(p-chlorophenyl)-1-(p-nitrobenzoyl)-5-(trifluoromethyl)pyrrole-3-carbonitrile M.P. 128–132° C.; |
| 8 | 4-bromo-1-(p-chlorobenzoyl)-2-(p-chlorophenyl)-5-(trifluoromethyl)pyrrole-3-carbonitrile M.P. 115–117° C.; |
| 9 | 1-benzoyl-4-bromo-2-chloro-5-(p-chlorophenyl)pyrrole-3-carbonitrile M.P. 179–181° C.; |
| 10 | 4-bromo-2-(p-chlorophenyl)-1-(1-naphthoyl)-5-(trifluoromethyl)pyrrole-3-carbonitrile M.P. 101–108° C.; |
| 11 | 4-bromo-2-(p-chlorophenyl)-1-(m-fluorobenzoyl)-5-(trifluoromethyl)pyrrole-3-carbonitrile M.P. 111–118° C.; |
| 12 | 4-bromo-2-(p-chlorophenyl)-1-(3,4-dichlorobenzoyl)-5-(trifluoromethyl)pyrrole-3-carbonitrile M.P. 135–144° C.; |
| 13 | 4-bromo-1-(p-tert-butylbenzoyl)-2-(p-chlorophenyl)-5-(trifluoromethyl)pyrrole-3-carbonitrile M.P. 113–115.5° C.; |
| 14 | 1-benzoyl-4-bromo-2-(p-bromophenyl)-5-(trifluoromethyl)pyrrole-3-carbonitrile M.P. 112–117° C.; |
| 15 | 1-benzoyl-2,4-dichloro-5-(3,4-dichlorophenyl)pyrrole-3-carbonitrile M.P. 107–110° C.; |
| 16 | 1-benzoyl-2,4-dichloro-5-(2-naphthyl)-pyrrole-3-carbonitrile M.P. 168–173.5° C.; |
| 17 | 4-bromo-2-(p-chlorophenyl)-1-(6-chloronicotinoyl)-5-(trifluoromethyl)pyrrole-3-carbonitrile M.P. 113–115° C.; |
| 18 | 4-bromo-2-(o-chlorophenyl)-1-picolinoyl-5-(trifluoromethyl)pyrrole-3-carbonitrile M.P. 114–116° C.; |
| 19 | 1-benzoyl-4-bromo-2-(3,4-difluorophenyl)-5-(trifluoromethyl)pyrrole-3-carbonitrile M.P. 72–88° C.; or |
| 20 | 1-benzoyl-4,5-dichloro-2-(α,α,α-trifluoro-p-tolyl)pyrrole-3-carbonitrile. |

TABLE I

Insecticidal and Acaricidal Evaluation of N-acylated Arylpyrroles

| Compound Number | Budworm 3rd ppm | | | Armyworm Day 3 ppm | | | | Armyworm Day 5 ppm | | | | S. Corn Rootworm ppm | | | Op Resistant Mites Adult ppm | | | Op Resistant Mites Egg ppm | | | Op Resistant Mites Nymph ppm | | | Leafhopper Cont. ppm | | | Roach Residual ppm | | |
|---|---|---|---|---|---|---|---|---|---|---|---|---|---|---|---|---|---|---|---|---|---|---|---|---|---|---|---|---|---|
| | 1000 | 100 | 10 | 1000 | 100 | 10 | RESi | 1000 | 100 | 10 | RESi | 50 | 10 | 1 | 300 | 100 | 10 | 300 | 100 | 10 | 300 | 100 | 10 | 100 | 10 | 1 | 1000 | 100 | 10 |
| 1 | 9 | 9 | 8 | 9 | 9 | 9 | 9 | 9 | 9 | 9 | 9 | 9 | 5 | 4 | 9 | 9 | 9 | 0 | 9 | 9 | 9 | — | — | 9 | 9 | 6 | 9 | 9 | 7 |
| 2 | 0 | 0 | 1 | 9 | 9 | 9 | 9 | 9 | 9 | 9 | 9 | 9 | 9 | 8 | 9 | 9 | 9 | 9 | 9 | 8 | x | — | 9 | 9 | 9 | 0 | 9 | 9 | 3 |
| 3 | 9 | 9 | 6 | 9 | 9 | 9 | 9 | 9 | 9 | 9 | 9 | 9 | 7 | 0 | 9 | 9 | 9 | 0 | 9 | 9 | 0 | — | — | 9 | 9 | 0 | 9 | 6 | 6 |
| 4 | 9 | 9 | 7 | 9 | 0 | 0 | 9 | 9 | 9 | 9 | 9 | 9 | 6 | 0 | 9 | 9 | 9 | 0 | 9 | 9 | 9 | — | — | 9 | 9 | 0 | 9 | 9 | 8 |
| 5 | 9 | 9 | 5 | 9 | 9 | 9 | 9 | 9 | 9 | 9 | 9 | 9 | 8 | 0 | | 0 | 0 | | 9 | 9 | | — | — | 9 | 9 | 0 | 9 | 9 | 6 |
| 6 | 9 | 9 | 9 | 9 | 9 | 9 | 9 | 9 | 9 | 9 | 9 | 9 | 5 | 0 | 9 | 9 | 9 | 9 | 9 | 9 | 0 | — | — | 9 | 8 | 0 | 9 | 9 | 0 |
| 7 | 9 | 9 | 8 | 9 | 9 | 9 | 9 | 9 | 9 | 9 | 9 | 9 | 4 | 0 | 9 | 9 | 9 | 0 | 9 | 8 | 0 | — | 9 | 9 | 9 | 9 | 9 | 7 | 0 |
| 8 | | 9 | 5 | 9 | 9 | 9 | 9 | 9 | 9 | 9 | 9 | 9 | 9 | 5 | 9 | 9 | 9 | 0 | 9 | 0 | 0 | — | 8 | | 0 | 0 | | 2 | 0 |
| 9 | 9 | 9 | 0 | 9 | 9 | 9 | 9 | 9 | 9 | 9 | 9 | 9 | | | | | | | | | | | | | 0 | | | 9 | |
| 10 | 9 | 9 | 4 | 9 | 9 | 9 | 9 | 9 | 9 | 9 | 9 | 9 | 9 | 0 | 0 | | 9 | 9 | | 8 | 6 | | 0 | 0 | 9 | 9 | 0 | 9 | |
| 11 | 9 | 9 | 9 | 9 | 9 | 9 | 9 | 9 | 9 | 9 | 9 | 9 | 9 | 6 | 0 | | 9 | 9 | | 9 | 0 | | — | 0 | 9 | 9 | 0 | 9 | 9 |
| 12 | 9 | 9 | 9 | 9 | 9 | 9 | 9 | 9 | 9 | 9 | 9 | 9 | 4 | 0 | 9 | 9 | 0 | 9 | 9 | 0 | 0 | — | 0 | 9 | 9 | 0 | 9 | 5 | 0 |
| 13 | 9 | 9 | 2 | 9 | 9 | 9 | 9 | 9 | 9 | 9 | 9 | 9 | 5 | 0 | 9 | 9 | 7 | 0 | 9 | 9 | 9 | * | * | 9 | 9 | 4 | 9 | 4 | 0 |
| 14 | 9 | 9 | 7 | 9 | 9 | 9 | 9 | 9 | 9 | 9 | 9 | 9 | 5 | 0 | | 9 | 9 | | 9 | 8 | | | 9 | 9 | 9 | 0 | 9 | | |
| 15 | 9 | 9 | 0 | 9 | 9 | 0 | 9 | 9 | 9 | 3 | 9 | 0 | | | 9 | 9 | 0 | 0 | 9 | 8 | 0 | — | 7 | 9 | 9 | | | | |
| 16 | | | | 9 | | | | 9 | | | | 0 | | | 0 | | | 0 | | | 0 | | | | | | | | |
| 17 | 9 | 9 | 9 | 9 | 9 | 9 | 9 | 9 | 9 | 9 | 9 | 0 | | | 9 | 9 | 9 | 9 | 9 | 0 | — | — | 8 | 0 | 0 | | | | |
| 18 | 9 | 9 | 9 | 9 | 9 | 9 | 9 | 9 | 9 | 9 | 9 | 9 | 9 | 0 | 0 | | | 0 | | | 0 | | | 9 | 9 | 0 | | | |
| 19 | | 9 | 0 | 9 | 9 | 0 | 9 | 9 | 0 | | 0 | | | 0 | | | 0 | | | 0 | | | 9 | 9 | 0 | | | | |

TABLE I-continued

Insecticidal and Acaricidal Evaluation of N-acylated Arylpyrroles

| Compound Number | Budworm 3rd ppm | Armyworm Day 3 ppm | Armyworm Day 5 ppm | S. Corn Rootworm ppm | Op Resistant Mites Adult ppm | Op Resistant Mites Egg ppm | Op Resistant Mites Nymph ppm | Leafhopper Cont. ppm | Roach Residual ppm |
|---|---|---|---|---|---|---|---|---|---|
| 20 | 9 9 2 | 9 9 9 9 | 9 9 9 9 | 0 | 0 9 9 | 0 9 0 | 9 — 8 | 9 9 0 | |

What we claim is:

1. An N-acylated arylpyrrole compound represented by the structural formula I:

(I)

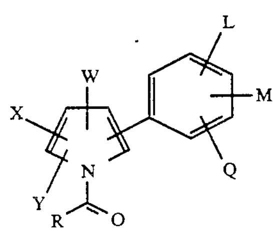

wherein

X is F, Cl, Br, I or $CF_3$;

Y is F, Cl, Br, I or $CF_3$;

W is CN or $NO_2$;

L is H, F, Cl or Br;

M and Q are each independendently H, $C_1$–$C_3$ alkyl, $C_1$–$C_3$ alkoxy, $C_1$–$C_3$ alkylthio $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$;

and when M and Q are attached to adjacent carbon atoms in the phenyl ring and taken with the carbon atoms to which they are attached, they may form a ring in which MQ represents the structure:

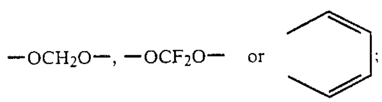

Z is S(o)n or O;

$R_1$ is H, F, $CHF_2$, CHFCl or $CF_3$;

$R_2$ is $C_1$–$C_3$ alkyl, $C_1$–$C_3$ alkoxy or $NR_3R_4$;

$R_3$ is H or $C_1$–$C_3$ alkyl;

$R_4$ is H, $C_1$–$C_3$ alkyl or $R_5CO$;

$R_5$ is H or $C_1$–$C_3$ alkyl;

n is an integer of 0, 1 or 2; and

R is phenyl optionally substituted with one to three halogen atoms, one to three $C_1$–$C_4$ alkyl groups, one $C_5$–$C_{12}$ alkyl group, one to two $C_1$–$C_4$ alkoxy groups, or one phenoxy, $C_1$–$C_4$ alkylthio, trialkylsilyl, $C_1$–$C_4$ alkylsulfinyl, $C_1$–$C_4$ alkylsulfonyl, carbo-$C_1$–$C_4$-alkoxy, carboxy, $CF_3$, CN, $NO_2$, di($C_1$–$C_4$ alkyl)amino or $C_1$–$C_4$ alkanoylamino;

1- or 2-naphthyl;

2-, 3- or 4-pyridyl optionally substituted with one to three halogen atoms; or a heteroaromatic 5-membered ring containing an oxygen, nitrogen, or a sulfur atom optionally substituted with one to three halogen atoms.

2. The compound according to claim 1 wherein R is phenyl optionally substituted with one to three halogen atoms, one to three $C_1$–$C_4$ alkyl groups, one to two $C_1$–$C_4$ alkoxy groups, or one $C_1$–$C_4$ alkylthio, trialkylsilyl, carbo-$C_1$–$C_4$-alkoxy, carboxy, $CF_3$, CN, $NO_2$ or di($C_1$–$C_4$ alkyl) amino;

1-naphthyl or 2-naphthyl;

2- or 3-furyl; or

2-, 3- or 4-pyridyl optionally substituted with one to three halogen atoms.

3. The compound according to claim 2 wherein the compound has the formula

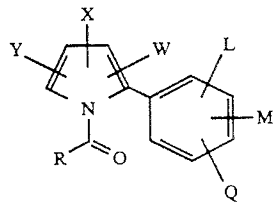

4. The compound according to claim 1, 1-benzoyl-4-bromo-2-(p-chlorophenyl)-5-(trifluoromethyl) pyrrole-3-carbonitrile.

5. The compound according to claim 1, 4-bromo-2-(p-chlorophenyl)-1-o-toluoyl-5-(trifluoromethyl) pyrrole-3-carbonitrile or 4-bromo-1-(m-chlorobenzoyl)-2-(p-chlorophenyl)-5-(trifluoromethyl) pyrrole-3-carbonitrile.

6. The compound according to claim 1, 4-bromo-2-(p-chlorophenyl)-1-(2-furoyl)-5-(trifluoromethyl) pyrrole-3-carbonitrile or 4-bromo-2-(p-chlorophenyl)-1-p-toluoyl-5-(trifluoromethyl)pyrrole-3-carbonitrile.

7. The compound according to claim 1, 4-bromo-2-(p-chlorophenyl)-5-(trifluoromethyl)-1-(α,α,α-trifluoro p-toluoyl)pyrrole-3-carbonitrile or 4-bromo-2-(p-chlorophenyl)-1-(p-nitrobenzoyl)-5-(trifluoromethyl) pyrrole-3-carbonitrile.

8. The compound according to claim 1, 4-bromo-1-(p-tert-butylbenzoyl)-2-(p-chlorophenyl)-5-(trifluoromethyl)pyrrole-3-carbonitrile or 4-bromo-2-(p-chlorophenyl)-1-(m-fluorobenzoyl)-5-(trifluoromethyl) pyrrole-3-carbonitrile.

9. A method for controlling insects, which comprises contacting said insects, their breeding grounds, food supply or habitat with an insecticidally, effective amount of an N-acylated arylpyrrole compound represented by the structural formula I:

(I)

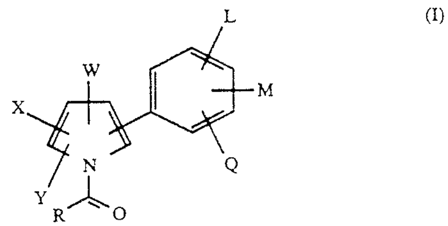

wherein

X is F, Cl, Br, I or $CF_3$;

Y is F, Cl, Br, I or $CF_3$;

W is CN or $NO_2$;

L is H, F, Cl or Br;

M and Q are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$;

and when M and Q are attached to adjacent carbon atoms in the phenyl ring and taken with the carbon atoms to which they are attached they may form a ring in which MQ represents the structure:

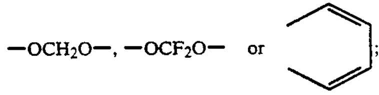

Z is S(O)n or O;

$R_1$ is H, F, $CHF_2$, CHFCl or $CF_3$;

$R_2$ is $C_1$–$C_3$ alkyl, $C_1$–$C_3$ alkoxy or $NR_3R_4$;

$R_3$ is H or $C_1$–$C_3$ alkyl;

$R_4$ is H, $C_1$–$C_3$ alkyl or $R_5CO$;

$R_5$ is H or $C_1$–$C_3$ alkyl;

n is an integer of 0, 1 or 2; and

R is phenyl optionally substituted with one to three halogen atoms, one or two $C_1$–$C_4$ alkyl groups, one $C_5$–$C_{12}$ alkyl group, one to two $C_1$–$C_4$ alkoxy groups, or one phenoxy, $C_1$–$C_4$ alkylthio, trialkylsilyl, $C_1$–$C_4$ alkylsulfinyl, $C_1$–$C_4$ alkylsulfonyl, carbo-$C_1$–$C_4$-alkoxy, carboxy, $CF_3$, CN, $NO_2$, di($C_1$–$C_4$ alkyl)amino or $C_1$–$C_4$ alkanoylamino;

1- or 2-naphthyl;

2-, 3- or 4-pyridyl optionally substituted with one to three halogen atoms; or a heteroaromatic 5-membered ring containing an oxygen, nitrogen, or a sulfur atom, and optionally substituted with one to three halogen atoms.

10. The method according to claim 9 wherein said formula I N-acylated arylpyrrole is applied to said insect, their breeding grounds, food supply or habitat in sufficient amount to provide a rate of from 0.1 kg/ha to about 4.0 kg/ha of active ingredient.

11. The method according to claim 9, wherein said N-acylated arylpyrrole has the formula

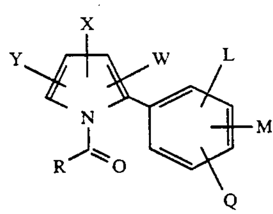

and wherein R is phenyl optionally substituted with one to three halogen atoms, one to three $C_1$–$C_4$ alkyl groups, one to two $C_1$–$C_4$ alkoxy groups, or one $C_1$–$C_4$ alkylthio, trialkylsilyl, carbo-$C_1$–$C_4$-alkoxy, carboxy, $CF_3$, CN, $NO_2$ or di($C_1$–$C_4$ alkyl)amino;

1-naphthyl or 2-naphthyl;

2- or 3-furyl; or

2-, 3- or 4-pyridyl optionally substituted with one to three halogen atoms.

12. The method according to claim 9, wherein the N-acylated arylpyrrole is 1-benzoyl-4-bromo-2-(p-chlorophenyl)-5-(trifluoromethyl)pyrrole3-carbonitrile.

13. The method according to claim 9, wherein the N-acylated arylpyrrole is 4-bromo-2-(p-chlorophenyl)-1-o-toluoyl-5-(trifluoromethyl)pyrrole 3-carbonitrile or 4-bromo-2-(p-chlorophenyl)-1-(p-nitrobenzoyl)-5-(trifluoromethyl)pyrrole 3-carbonitrile.

14. A method for protecting growing plants from attack by insects, which comprises applying to the foliage of said plants or to the soil or water in which they are growing, an insecticidally, effective amount of an N-acylated arylpyrrole having the structure:

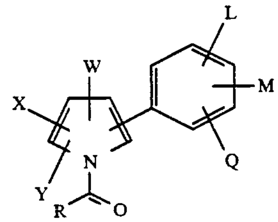

wherein

X is F, Cl, Br, I or $CF_3$;

Y is F, Cl, Br, I or $CF_3$;

W is CN or $NO_2$;

L is H, F, Cl or Br;

M and Q are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$;

and when M and Q are attached to adjacent carbon atoms in the phenyl ring and taken with the carbon atoms to which they are attached they may form a ring in which MQ represents the structure:

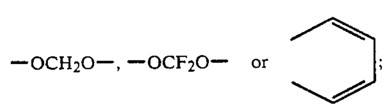

Z is S(O)n or O;

$R_1$ is H, F, $CHF_2$, CHFCl or $CF_3$;

$R_2$ is $C_1$–$C_3$ alkyl, $C_1$–$C_3$ alkoxy or $NR_3R_4$;

$R_3$ is H or $C_1$–$C_3$ alkyl;

$R_4$ is H, $C_1$–$C_3$ alkyl or $R_5CO$;

$R_5$ is H or $C_1$–$C_3$ alkyl;

n is an integer of 0, 1 or 2; and

R is phenyl optionally substituted with one to three halogen atoms, one or two $C_1$–$C_4$ alkyl groups, one $C_5$–$C_{12}$ alkyl group, one to two $C_1$–$C_4$ alkoxy groups, or one phenoxy, $C_1$–$C_4$ alkylthio, trialkylsilyl, $C_1$–$C_4$ alkylsulfinyl, $C_1$–$C_4$ alkylsulfonyl, carbo-$C_1$–$C_4$-alkoxy, carboxy, $CF_3$, CN, $NO_2$, di($C_1$–$C_4$ alkyl)amino or $C_1$–$C_4$ alkanoylamino;

1- or 2-naphthyl;

2-, 3- or 4-pyridyl optionally substituted with one to three halogen atoms; or a heteroaromatic 5-membered ring containing an oxygen, nitrogen, or a sulfur atom, and optionally substituted with one to three halogen atoms.

15. The method according to claim 14, wherein said N-acylated arylpyrrole is applied to plant foliage or the soil in which said plants are growing, in the form of a dilute spray containing from about 10 ppm to 10,000 ppm of said N-acylated arylpyrrole.

16. The method according to claim 14, wherein said N-acylated arylpyrrole is applied to plant foliage or the soil or water in which they are growing in sufficient amount to provide about 0.1 kg/ha to about 4.0 kg/ha of said N-acylated arylpyrrole.

17. The method according to claim 14, wherein said N-acylated arylpyrrole is:

1-benzoyl-4-bromo-2-(p-chlorophenyl)-5-(trifluoromethyl)pyrrole-3-carbonitrile;
4-bromo-2-(p-chlorophenyl)-1-o-toluoyl-5-(trifluoromethyl)pyrrole-3-carbonitrile;
4-bromo-1-(m-chlorobenzoyl)-2-(p-chlorophenyl)-5-(trifluoromethyl)pyrrole-3-carbonitrile;
4-bromo-2-(p-chlorophenyl)-1-(2-furoyl)-5-(trifluoromethyl)pyrrole-3-carbonitrile;
4-bromo-2-(p-chlorophenyl)-1-p-toluoyl-5-(trifluoromethyl)pyrrole-3-carbonitrile;
4-bromo-2-(p-chlorophenyl)-5-(trifluoromethyl)-1-($\alpha$,$\alpha$,-$\alpha$-trifluoro-p-toluoyl)pyrrole-3-carbonitrile;
4-bromo-2-(p-chlorophenyl)-1-(p-nitrobenzoyl)-5-(trifluoromethyl)pyrrole-3-carbonitrile;
4-bromo-1-(p-chlorobenzoyl)-2-(p-chlorophenyl)-5-(trifluoromethyl)pyrrole-3-carbonitrile;
1-benzoyl-4-bromo-2-chloro-5-(p-chlorophenyl)pyrrole-3-carbonitrile;
4-bromo-2-(p-chlorophenyl)-1-(1-naphthoyl)-5-(trifluoromethyl)pyrrole-3-carbonitrile;
4-bromo-2-(p-chlorophenyl)-1-(m-fluorobenzoyl)-5-(trifluoromethyl)pyrrole-3-carbonitrile;
4-bromo-2-(p-chlorophenyl)-1-(3,4-dichlorobenzoyl)-5-(trifluoromethyl)pyrrole-3-carbonitrile;
4-bromo-1-(p-tert-butylbenzoyl)-2-(p-chlorophenyl)-5-(trifluoromethyl)pyrrole-3-carbonitrile; or
1-benzoyl-4-bromo-2-(p-bromophenyl)-5-(trifluoromethyl)pyrrole-3-carbonitrile.

* * * * *